(12) United States Patent
Spence et al.

(10) Patent No.: US 10,421,766 B2
(45) Date of Patent: Sep. 24, 2019

(54) BISAMINOALKOXYSILANE COMPOUNDS AND METHODS FOR USING SAME TO DEPOSIT SILICON-CONTAINING FILMS

(71) Applicant: Air Products and Chemicals, Inc., Allentown, PA (US)

(72) Inventors: Daniel P. Spence, Carlsbad, CA (US); Xinjian Lei, Vista, CA (US); Ronald Martin Pearlstein, San Marcos, CA (US); Manchao Xiao, San Diego, CA (US); Jianheng Li, Emmaus, PA (US)

(73) Assignee: VERSUM MATERIALS US, LLC, Tempe, AZ (US)

( * ) Notice: Subject to any disclaimer, the term of this patent is extended or adjusted under 35 U.S.C. 154(b) by 513 days.

(21) Appl. No.: 15/017,913

(22) Filed: Feb. 8, 2016

(65) Prior Publication Data

US 2016/0237100 A1   Aug. 18, 2016

Related U.S. Application Data

(60) Provisional application No. 62/115,729, filed on Feb. 13, 2015.

(51) Int. Cl.
| | |
|---|---|
| *C07F 7/10* | (2006.01) |
| *C07F 7/18* | (2006.01) |
| *C01B 21/082* | (2006.01) |
| *C01B 33/18* | (2006.01) |
| *C23C 16/30* | (2006.01) |
| *C23C 16/455* | (2006.01) |
| *C01B 32/90* | (2017.01) |
| *C09D 7/63* | (2018.01) |
| *C08L 83/04* | (2006.01) |
| *C09D 4/00* | (2006.01) |
| *C09D 183/08* | (2006.01) |
| *C08G 77/26* | (2006.01) |

(52) U.S. Cl.
CPC ............ *C07F 7/10* (2013.01); *C01B 21/0823* (2013.01); *C01B 21/0828* (2013.01); *C01B 32/90* (2017.08); *C01B 33/181* (2013.01); *C07F 7/1804* (2013.01); *C07F 7/188* (2013.01); *C08L 83/04* (2013.01); *C09D 4/00* (2013.01); *C09D 7/63* (2018.01); *C09D 183/08* (2013.01); *C23C 16/308* (2013.01); *C23C 16/45553* (2013.01); *C08G 77/26* (2013.01)

(58) Field of Classification Search
CPC .......... C07F 7/10; C07F 7/1804; C07F 7/188; C01B 32/90; C01B 21/0823; C01B 21/0828; C01B 33/181; C09D 7/63; C09D 4/00; C09D 183/08; C23C 16/308; C23C 16/45553; C08L 83/04; C08G 77/26
See application file for complete search history.

(56) References Cited

U.S. PATENT DOCUMENTS

| | | |
|---|---|---|
| 3,458,556 A | 7/1969 | Di Paola |
| 4,345,088 A | 8/1982 | Vick et al. |
| 4,491,669 A | 1/1985 | Arkles et al. |
| 6,114,558 A | 9/2000 | Larson et al. |
| 7,425,350 B2 | 9/2008 | Todd |
| 7,524,735 B1 | 4/2009 | Gauri et al. |
| 7,582,555 B1 | 9/2009 | Lang et al. |
| 7,629,227 B1 | 12/2009 | Wang et al. |
| 7,888,233 B1 | 2/2011 | Gauri et al. |
| 7,888,273 B1 | 2/2011 | Wang et al. |
| 7,915,139 B1 | 3/2011 | Lang et al. |
| 7,943,531 B2 | 5/2011 | Nemani et al. |
| 8,187,951 B1 | 5/2012 | Wang et al. |
| 9,245,739 B2 | 1/2016 | Ndiege et al. |
| 2010/0164057 A1* | 7/2010 | Hunks ............... H01L 21/02123 257/520 |
| 2015/0004806 A1 | 1/2015 | Ndiege et al. |

FOREIGN PATENT DOCUMENTS

| | | |
|---|---|---|
| KR | 20080042876 A | 5/2008 |
| KR | 20130087445 A | 8/2013 |
| KR | 20140075634 A | 6/2014 |
| WO | 0042049 | 7/2000 |
| WO | 2004012874 | 2/2004 |
| WO | 2006129773 | 12/2006 |

OTHER PUBLICATIONS

Bauer, J., "One-step conversion of methoxysilanes to aminosilanes: a convenient synthetic strategy to N,O-functionalised organosilanes", Chemical Communications, 2012, 48(57) pp. 7212-7214.
Szilvasi, T., et al., "Unique Insertion Mechanisms of Bis-dehydro-B-diketiminato Silylene", Organometallics, 2011, 30(20), pp. 5344-5351.
Tomasik, A., et al., "Synthesis and Reactivity of Three New N-Heterocyclic Silylenes", Organometallics, 2009, 28(1), pp. 378-381.
Li, W., et al., "A New Monomeric Saturated N-Heterocyclic Silylene as a Racemic Mixture", Organometallics, 2006, 25(16), pp. 3802-3805.

(Continued)

*Primary Examiner* — Robert S Walters, Jr.
(74) *Attorney, Agent, or Firm* — Rosaleen P. Morris-Oskanian; David K. Benson

(57) ABSTRACT

Bisaminoalkoxysilanes of Formula I, and methods using same, are described herein:

$$R^1Si(NR^2R^3)(NR^4R^5)OR^6 \qquad I$$

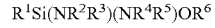

where $R^1$ is selected from hydrogen, a $C_1$ to $C_{10}$ linear alkyl group, a $C_3$ to $C_{10}$ branched alkyl group, a $C_3$ to $C_{10}$ cyclic alkyl group, a $C_3$ to $C_{10}$ alkenyl group, a $C_3$ to $C_{10}$ alkynyl group, a $C_4$ to $C_{10}$ aromatic hydrocarbon group; $R^2$, $R^3$, $R^4$, and $R^5$ are each independently selected from hydrogen, a $C_4$ to $C_{10}$ branched alkyl group, a $C_3$ to $C_{10}$ cyclic alkyl group, a $C_3$ to $C_{10}$ alkenyl group, a $C_3$ to $C_{10}$ alkynyl group, and a $C_4$ to $C_{10}$ aromatic hydrocarbon group; $R^6$ is selected from a $C_1$ to $C_{10}$ linear alkyl group, a $C_3$ to $C_{10}$ branched alkyl group, a $C_3$ to $C_{10}$ cyclic alkyl group, a $C_3$ to $C_{10}$ alkenyl group, a $C_2$ to $C_{10}$ alkynyl group, and a $C_4$ to $C_{10}$ aromatic hydrocarbon group.

13 Claims, No Drawings

(56) References Cited

OTHER PUBLICATIONS

Gaspar, P., et al., "Product Subclass 3: Silylenes", Science of Synthesis, 202, 4, pp. 135-158.
Heinicke, J., et al., "Zur Themie der Silylene: Cycloadditionen von Methoxymethylsilylen mit Heterodiene", Journal of Organometallic Chemistry, 1992, 423(1), pp. 13-21.
Kupce, E., et al., "Indirect Nuclear Spin-Spin Coupling Constants of Nitrogen-15 to Silicon-29 in Silylamines", Journal of the Chemical Society, Chemical Communications, 1984, (9), pp. 581-582.
Anon., "Cyclic precursors for gap fill depositions of SiO2 in trenches in microelectronics fabrication using silicon containing compounds", IP.COM Journal, IPCOM000193876D, Mar. 11, 2010.
Suen, Linda M., et al, "A new and more powerfully activating diamine for practical and scalable enantioselective aldehyde crotylsilylation reactions", Chemical Science, 2013, 2413.
Zark, P., et al, "Synthesis and reactivity of N-aryl substituted N-heterocyclic silylenes", Journal of Organometallic Chemistry, 2010, 398-408.
Kupce, Eriks, et al, "Natrual abundance studies of silicon-29 to nitrogen-15 coupling constants", Journal of Magnetic Resonance, 1988, 63-73.
Uhlig, Wolfram, et al, "Zur Synthese und reaktivitaet aminofunktioneller silyltriflate", Journal of Organometallic Chemistry, 1994, 31-35.
Haaf, Michael, et al, "Synthesis and reactivity of the stable silylene N,N'-di-tert-butyl-1,3-diaza-2-sila-2-ylidene", Canadian Journal of Chemistry, 2000, 1526-1533.
Underiner, Gail E., et al, "Silaamidide Salts: Synthesis, structure, and reactions", Journal of the American Chemical Society, 1991, 8437-8443.
Dielkus, Sven, et al, "Synthese und Kristallstruktur des 2,4-Di-tert-butoxy-2,4-di-tert-butylcyclodisilazans", Zeitschrift fuer Naturforschung, 1995, 844-847.
Van Wazer, J.R., et al, "Scrambling of methoxyl, dimethylamino and chloro groups on the methyl- and dimethylsilicon moieties", J. Inorg. Nucl. Chem., 1964, 737-744.
Larry L. Hench et al, "The Sol-Gel Process", American Chemical Society, 1990, 33-72.

* cited by examiner

BISAMINOALKOXYSILANE COMPOUNDS AND METHODS FOR USING SAME TO DEPOSIT SILICON-CONTAINING FILMS

CROSS-REFERENCE TO RELATED APPLICATIONS

This application claims the priority benefit of U.S. Provisional Application No. 62/115,729, filed Feb. 13, 2015. The disclosure of this provisional application is hereby incorporated by reference in its entirety.

BACKGROUND OF THE INVENTION

Described herein are volatile and thermally stable aminoalkoxysilanes, more specifically bisaminoalkoxysilanes, and methods for using same to deposit stoichiometric or non-stoichiometric silicon-containing films such as, but not limited to, silicon oxide, silicon nitride, silicon oxynitride, silicon carboxide, and silicon oxycarbonitride films.

U.S. Pat. No. 4,491,669 discloses the preparation of pure mixed alkoxyaminosilanes corresponding to the general formula: $R_mSi(OR')_n(NR''R''')_p$ wherein: R is hydrogen, short chain alkyl or alkenyl or aryl; R'' and R''' are separately either hydrogen, short chain alkyl or aryl, at least one being other than hydrogen; R' is short chain alkyl or aryl; and m, n and p are integers such that m+n+p=4 and n and p are at least one each. The obtained compounds are employed in end-capping of polysiloxanes having terminal silane groups.

U.S. Pat. No. 4,345,088 discloses compounds having the formula $(R)_2NXSiHOR$ where X is OR or $N(R)_2$ and wherein R is an alkyl of from one to eight carbon atoms. These compounds are prepared by treating tris(dialkylamino)hydridosilanes with alkanols.

U.S. Pat. No. 6,114,558 discloses the preparation of alkyl(amino)dialkoxysilanes having the general formula $RSi(NR^1R^2)(OR^3)_2$, wherein R is a straight or branched chain alkyl of 1 to 20 carbon atoms, an arylalkyl or aryl radical, $R^1$ and $R^2$ are alkyl radicals of 1 to 6 carbon atoms and one of them can be hydrogen, and $R^3$ is an alkyl radical of 1-6 carbon atoms with methyl being preferred. The alkyl(amino)dialkoxysilanes are prepared by anhydrously reacting stoichiometric amounts of an alkoxysilane and an alkylaminomagnesium chloride in a reverse addition process. The alkylamino magnesium chloride is preferably prepared in situ by the reaction of a Grignard reagent (RMX) and an alkylamine in a suitable aprotic solvent, such as tetrahydrofuran (THF). The reaction can be conducted in a temperature range of from 25°-75° C., without a catalyst, and the aprotic solvent is recovered for re-use in the process. Thus, reaction of isopropylmagnesium chloride with tert-butylamine in THF followed by treatment with methyltrimethoxysilane gave 82% methyl(tert-butylamino)dimethoxysilane.

U.S. Pat. No. 7,524,735 discloses a method related to filling gaps on substrates with a solid dielectric material by forming a flowable film in the gap. The flowable film provides a consistent, void-free gap fill. The film is then converted to a solid dielectric material. In this manner gaps on the substrate are filled with a solid dielectric material. According to various embodiments, the methods involve reacting a dielectric precursor with an oxidant to form the dielectric material. In certain embodiments, the dielectric precursor condenses and subsequently reacts with the oxidant to form dielectric material. In certain embodiments, vapor phase reactants react to form a condensed flowable film.

U.S. Pat. No. 7,943,531 discloses a method of depositing a silicon oxide layer over a substrate in a deposition chamber. A first silicon-containing precursor, a second silicon-containing precursor and a $NH_3$ plasma are reacted to form a silicon oxide layer. The first silicon-containing precursor includes at least one of Si—H bond and Si—Si bond. The second silicon-containing precursor includes at least one Si—N bond.

U.S. Pat. No. 7,425,350 discloses a method for making a Si-containing material which comprises transporting a pyrolyzed Si-precursor to a substrate and polymerizing the pyrolyzed Si-precursor on the substrate to form a Si-containing film. Polymerization of the pyrolyzed Si-precursor may be carried out in the presence of a porogen to thereby form a porogen-containing Si-containing film. The porogen may be removed from the porogen-containing, Si-containing film to thereby form a porous Si-containing film. Preferred porous Si-containing films have low dielectric constants and thus are suitable for various low-k applications such as in microelectronics and microelectromechanic systems.

U.S. Pat. No. 7,888,273 discloses methods of lining and/or filling gaps on a substrate by creating flowable silicon oxide-containing films are provided. The methods involve introducing vapor-phase silicon-containing precursor and oxidant reactants into a reaction chamber containing the substrate under conditions such that a condensed flowable film is formed on the substrate. The flowable film at least partially fills gaps on the substrates and is then converted into a silicon oxide film. In certain embodiments the methods involve using a catalyst e.g. a nucleophile or onium catalyst in the formation of the film. The catalyst may be incorporated into one of the reactants and/or introduced as a separate reactant. Also provided are methods of converting the flowable film to a solid dielectric film. The methods of this invention may be used to line or fill high aspect ratio gaps including gaps having aspect ratios ranging from 3:1 to 10:1.

U.S. Pat. No. 7,629,227 discloses methods of lining and/or filling gaps on a substrate by creating flowable silicon oxide-containing films. The methods involve introducing vapor-phase silicon-containing precursor and oxidant reactants into a reaction chamber containing the substrate under conditions such that a condensed flowable film is formed on the substrate. The flowable film at least partially fills gaps on the substrates and is then converted into a silicon oxide film. In certain embodiments the methods involve using a catalyst e.g. a nucleophile or onium catalyst in the formation of the film. The catalyst may be incorporated into one of the reactants and/or introduced as a separate reactant. Also provided are methods of converting the flowable film to a solid dielectric film. The methods of this invention may be used to line or fill high aspect ratio gaps including gaps having aspect ratios ranging from 3:1 to 10:1.

WO 06129773 disclosed a catalyst for polymerization of olefins formed from (A) a solid catalyst component containing magnesium titanium halogen and an electron donor compound (B) an organoaluminum compound shown by the formula $R^6_pAlQ_{3-p}$ and (C) an aminosilane compound shown by the formula $R^3_nSi(NR^4R^5)_{4-n}$; and a process for producing a catalyst for polymerization of olefins in the presence of the catalyst are provided.

Thus, there is a need in the art to provide a precursor that can be used to deposit a silicon-containing film that provides one or more of the following advantages: low processing temperatures (e.g., 500° C. or below); a relatively good deposition rate ranging from about 0.1 nanometers (nm) to 1000 nm per minute; a compositional uniformity that deviates by no more than ±10% measured over multiple points on a wafer analyzed by Fourier FTIR or XPS; high stability (e.g., undergoing a degradation of no more than about 5% or less per year or no more than about 1% or less per year); flowability for filling trenches, gap, or vias as observed by scanning electron microcopy (SEM); and combinations thereof.

BRIEF SUMMARY OF THE INVENTION

Described herein are bisaminoalkoxysilane precursors and methods using same for forming stoichiometric or non-stoichiometric silicon-containing films, such as, but not limited to, silicon oxide, silicon carboxide, silicon nitride, silicon oxynitride, silicon carbide, silicon carbonitride, and combinations thereof onto at least a surface or portion of a substrate. Also disclosed herein are the methods to form silicon-containing films or coatings on an object to be processed, such as, for example, a semiconductor wafer.

In one aspect, there is provided a composition for depositing a silicon containing film comprising at least one bisaminoalkoxysilane having Formula I:

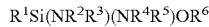

where $R^1$ is selected from a hydrogen atom, a $C_1$ to $C_{10}$ linear alkyl group, a $C_3$ to $C_{10}$ branched alkyl group, a $C_3$ to $C_{10}$ cyclic alkyl group, a $C_3$ to $C_{10}$ alkenyl group, a $C_3$ to $C_{10}$ alkynyl group, a $C_4$ to $C_{10}$ aromatic hydrocarbon group; $R^2$, $R^3$, $R^4$, and $R^5$ are each independently selected from a hydrogen atom, a $C_4$ to $C_{10}$ branched alkyl group, a $C_3$ to $C_{10}$ cyclic alkyl group, a $C_3$ to $C_{10}$ alkenyl group, a $C_3$ to $C_{10}$ alkynyl group, and a $C_4$ to $C_{10}$ aromatic hydrocarbon group; $R^6$ is selected from a $C_1$ to $C_{10}$ linear alkyl group, a $C_3$ to $C_{10}$ branched alkyl group, a $C_3$ to $C_{10}$ cyclic alkyl group, a $C_3$ to $C_{10}$ alkenyl group, a $C_2$ to $C_{10}$ alkynyl group, and a $C_4$ to $C_{10}$ aromatic hydrocarbon group; and optionally wherein $R^2$ and $R^3$, $R^4$ and $R^5$, or both in Formula I can be linked together to form a ring; and optionally wherein $R^2$ and $R^4$ in Formula I can be linked together to form a diamino group. Exemplary bisaminoalkoxysilane precursor compounds having Formula I include, but are not limited to, bis(tert-butylamino)methoxymethylsilane, bis(tert-butylamino)ethoxymethylsilane, bis(cis-2,6-dimethylpiperidino)methoxymethylsilane, and bis(cis-2,6-dimethylpiperidino)ethoxymethylsilane.

In another aspect, there is provided a method for forming a silicon-containing film on at least one surface of a substrate comprising:
  providing the substrate in a reactor; and
  forming the silicon-containing film on the at least one surface by a deposition process using at least one precursor comprising a bisaminoalkoxysilane having Formula I:

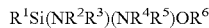

where $R^1$ is selected from a hydrogen atom, a $C_1$ to $C_{10}$ linear alkyl group, a $C_3$ to $C_{10}$ branched alkyl group, a $C_3$ to $C_{10}$ cyclic alkyl group, a $C_3$ to $C_{10}$ alkenyl group, a $C_3$ to $C_{10}$ alkynyl group, a $C_4$ to $C_{10}$ aromatic hydrocarbon group; $R^2$, $R^3$, $R^4$, and $R^5$ are each independently selected from a hydrogen atom, a $C_4$ to $C_{10}$ branched alkyl group, a $C_3$ to $C_{10}$ cyclic alkyl group, a $C_3$ to $C_{10}$ alkenyl group, a $C_3$ to $C_{10}$ alkynyl group, and a $C_4$ to $C_{10}$ aromatic hydrocarbon group; $R^6$ is selected from a $C_1$ to $C_{10}$ linear alkyl group, a $C_3$ to $C_{10}$ branched alkyl group, a $C_3$ to $C_{10}$ cyclic alkyl group, a $C_3$ to $C_{10}$ alkenyl group, a $C_2$ to $C_{10}$ alkynyl group, and a $C_4$ to $C_{10}$ aromatic hydrocarbon group; and optionally wherein $R^2$ and $R^3$, $R^4$ and $R^5$, or both in Formula I can be linked together to form a ring; and optionally wherein $R^2$ and $R^4$ in Formula I can be linked together to form a diamino group.

In another aspect, there is provided a method of forming a silicon oxide or carbon doped silicon oxide film via an atomic layer deposition process or cyclic chemical vapor deposition process, the method comprising the steps of:
  a. providing a substrate in a reactor;
  b. introducing into the reactor at least one precursor comprising a bisaminoalkoxysilane compound having Formula I:

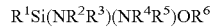

where $R^1$ is selected from a hydrogen atom, a $C_1$ to $C_{10}$ linear alkyl group, a $C_3$ to $C_{10}$ branched alkyl group, a $C_3$ to $C_{10}$ cyclic alkyl group, a $C_3$ to $C_{10}$ alkenyl group, a $C_3$ to $C_{10}$ alkynyl group, a $C_4$ to $C_{10}$ aromatic hydrocarbon group; $R^2$, $R^3$, $R^4$, and $R^5$ are each independently selected from a hydrogen atom, a $C_4$ to $C_{10}$ branched alkyl group, a $C_3$ to $C_{10}$ cyclic alkyl group, a $C_3$ to $C_{10}$ alkenyl group, a $C_3$ to $C_{10}$ alkynyl group, and a $C_4$ to $C_{10}$ aromatic hydrocarbon group; $R^6$ is selected from a $C_1$ to $C_{10}$ linear alkyl group, a $C_3$ to $C_{10}$ branched alkyl group, a $C_3$ to $C_{10}$ cyclic alkyl group, a $C_3$ to $C_{10}$ alkenyl group, a $C_2$ to $C_{10}$ alkynyl group, and a $C_4$ to $C_{10}$ aromatic hydrocarbon group; and optionally wherein $R^2$ and $R^3$, $R^4$ and $R^5$, or both in Formula I can be linked together to form a ring; and optionally wherein $R^2$ and $R^4$ in Formula I can be linked together to form a diamino group;
  c. purging the reactor with a purge gas;
  d. introducing an oxygen source into the reactor;
  e. purging the reactor with a purge gas; and
repeating the steps b through e until a desired thickness of the film is obtained.

In a further aspect, there is provided a method of forming a silicon oxide or carbon doped silicon oxide film onto at least a surface of a substrate using a CVD process comprising:
  a. providing a substrate in a reactor;
  b. introducing into the reactor at least one precursor comprising a bisaminoalkoxysilane compound having the following Formula I:

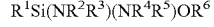

where $R^1$ is selected from a hydrogen atom, a $C_1$ to $C_{10}$ linear alkyl group, a $C_3$ to $C_{10}$ branched alkyl group, a $C_3$ to $C_{10}$ cyclic alkyl group, a $C_3$ to $C_{10}$ alkenyl group, a $C_3$ to $C_{10}$ alkynyl group, a $C_4$ to $C_{10}$ aromatic hydrocarbon group; $R^2$, $R^3$, $R^4$, and $R^5$ are each independently selected from a hydrogen atom, a $C_4$ to $C_{10}$ branched alkyl group, a $C_3$ to $C_{10}$ cyclic alkyl group, a $C_3$ to $C_{10}$ alkenyl group, a $C_3$ to $C_{10}$ alkynyl group, and a $C_4$ to $C_{10}$ aromatic hydrocarbon group; $R^6$ is selected from a $C_1$ to $C_{10}$ linear alkyl group, a $C_3$ to $C_{10}$ branched alkyl group, a $C_3$ to $C_{10}$ cyclic alkyl group, a $C_3$ to $C_{10}$ alkenyl group, a $C_2$ to $C_{10}$ alkynyl group, and a $C_4$ to $C_{10}$ aromatic hydrocarbon group; and optionally wherein $R^2$ and $R^3$, $R^4$ and $R^5$, or both in Formula I can be linked together to form a ring; and optionally wherein $R^2$ and $R^4$ in Formula I can be linked together to form a diamino group; and
  c. providing an oxygen source to deposit the silicon oxide or carbon doped silicon oxide film onto the at least one surface.

In another aspect, there is provided a method of forming a silicon nitride or silicon oxynitride or silicon carboxynitride film via an atomic layer deposition process or cyclic chemical vapor deposition process, the method comprising the steps of:

a. providing a substrate in a reactor;
b. introducing into the reactor an at least one precursor comprising a bisaminoalkoxysilane compound having Formula I:

$$R^1Si(NR^2R^3)(NR^4R^5)OR^6 \qquad I$$

where $R^1$ is selected from a hydrogen atom, a $C_1$ to $C_{10}$ linear alkyl group, a $C_3$ to $C_{10}$ branched alkyl group, a $C_3$ to $C_{10}$ cyclic alkyl group, a $C_3$ to $C_{10}$ alkenyl group, a $C_3$ to $C_{10}$ alkynyl group, a $C_4$ to $C_{10}$ aromatic hydrocarbon group; $R^2$, $R^3$, $R^4$, and $R^5$ are each independently selected from a hydrogen atom, a $C_4$ to $C_{10}$ branched alkyl group, a $C_3$ to $C_{10}$ cyclic alkyl group, a $C_3$ to $C_{10}$ alkenyl group, a $C_3$ to $C_{10}$ alkynyl group, and a $C_4$ to $C_{10}$ aromatic hydrocarbon group; $R^6$ is selected from a $C_1$ to $C_{10}$ linear alkyl group, a $C_3$ to $C_{10}$ branched alkyl group, a $C_3$ to $C_{10}$ cyclic alkyl group, a $C_3$ to $C_{10}$ alkenyl group, a $C_2$ to $C_{10}$ alkynyl group, and a $C_4$ to $C_{10}$ aromatic hydrocarbon group; and optionally wherein $R^2$ and $R^3$, $R^4$ and $R^5$, or both in Formula I can be linked together to form a ring; and optionally wherein $R^2$ and $R^4$ in Formula I can be linked together to form a diamino group;
c. purging the reactor with a purge gas;
d. introducing a nitrogen-containing source into the reactor;
e. purging the reactor with a purge gas; and
repeating the steps b through e until a desired thickness of the silicon nitride or silicon oxynitride or silicon carboxynitride film is obtained.

In a further aspect, there is provided a method of forming a silicon nitride or silicon oxynitride film onto at least a surface of a substrate using a CVD process comprising:
a. providing a substrate in a reactor;
b. introducing into the reactor at least one precursor comprising a bisaminoalkoxysilane compound having Formula I:

$$R^1Si(NR^2R^3)(NR^4R^5)OR^6 \qquad I$$

where $R^1$ is selected from a hydrogen atom, a $C_1$ to $C_{10}$ linear alkyl group, a $C_3$ to $C_{10}$ branched alkyl group, a $C_3$ to $C_{10}$ cyclic alkyl group, a $C_3$ to $C_{10}$ alkenyl group, a $C_3$ to $C_{10}$ alkynyl group, a $C_4$ to $C_{10}$ aromatic hydrocarbon group; $R^2$, $R^3$, $R^4$, and $R^5$ are each independently selected from a hydrogen atom, a $C_4$ to $C_{10}$ branched alkyl group, a $C_3$ to $C_{10}$ cyclic alkyl group, a $C_3$ to $C_{10}$ alkenyl group, a $C_3$ to $C_{10}$ alkynyl group, and a $C_4$ to $C_{10}$ aromatic hydrocarbon group; $R^6$ is selected from a $C_1$ to $C_{10}$ linear alkyl group, a $C_3$ to $C_{10}$ branched alkyl group, a $C_3$ to $C_{10}$ cyclic alkyl group, a $C_3$ to $C_{10}$ alkenyl group, a $C_2$ to $C_{10}$ alkynyl group, and a $C_4$ to $C_{10}$ aromatic hydrocarbon group; and optionally wherein $R^2$ and $R^3$, $R^4$ and $R^5$, or both in Formula I can be linked together to form a ring; and optionally wherein $R^2$ and $R^4$ in Formula I can be linked together to form a diamino group; and
c. providing a nitrogen-containing source wherein the at least one bisaminoalkoxysilane precursors and the nitrogen-containing source react to deposit the film comprising both silicon and nitrogen onto the at least one surface.

In another aspect, a vessel for depositing a silicon-containing film comprising one or more bisaminoalkoxysilane precursor compound having Formula I is described herein. In one particular embodiment, the vessel comprises at least one pressurizable vessel (preferably of stainless steel) fitted with the proper valves and fittings to allow the delivery of one or more precursors to the reactor for a CVD or an ALD process.

In yet another aspect, there is provided a composition for the deposition of a silicon-containing film comprising: at least one precursor comprising a bisaminoalkoxysilane compound having the following Formula I:

$$R^1Si(NR^2R^3)(NR^4R^5)OR^6 \qquad I$$

where $R^1$ is selected from a hydrogen atom, a $C_1$ to $C_{10}$ linear alkyl group, a $C_3$ to $C_{10}$ branched alkyl group, a $C_3$ to $C_{10}$ cyclic alkyl group, a $C_3$ to $C_{10}$ alkenyl group, a $C_3$ to $C_{10}$ alkynyl group, a $C_4$ to $C_{10}$ aromatic hydrocarbon group; $R^2$, $R^3$, $R^4$, and $R^5$ are each independently selected from a hydrogen atom, a $C_4$ to $C_{10}$ branched alkyl group, a $C_3$ to $C_{10}$ cyclic alkyl group, a $C_3$ to $C_{10}$ alkenyl group, a $C_3$ to $C_{10}$ alkynyl group, and a $C_4$ to $C_{10}$ aromatic hydrocarbon group; $R^6$ is selected from a $C_1$ to $C_{10}$ linear alkyl group, a $C_3$ to $C_{10}$ branched alkyl group, a $C_3$ to $C_{10}$ cyclic alkyl group, a $C_3$ to $C_{10}$ alkenyl group, a $C_2$ to $C_{10}$ alkynyl group, and a $C_4$ to $C_{10}$ aromatic hydrocarbon group; and optionally wherein $R^2$ and $R^3$, $R^4$ and $R^5$, or both in Formula I can be linked together to form a ring; and optionally wherein $R^2$ and $R^4$ in Formula I can be linked together to form a diamino group.

DETAILED DESCRIPTION OF THE INVENTION

Bisaminoalkoxysilane compounds are used as precursors to deposit stoichiometric and non-stoichiometric silicon containing films such as, but not limited to, silicon oxide, silicon oxycarbide, silicon nitride, silicon oxynitride and silicon oxycarbonitride using a variety of deposition processes. The bisaminoalkoxysilane precursors described herein are high purity (e.g., ranging from about 90% to about 99.9 or about 95% to 99% assay as measured by gas chromatography (GC)), volatile liquid precursors.

The precursors are typically vaporized and delivered to a deposition chamber or reactor as a gas to deposit a silicon containing film via various deposition techniques including, but not limited to, chemical vapor deposition (CVD), cyclic chemical vapor deposition (CCVD), plasma enhanced chemical vapor deposition (PECVD), flowable chemical vapor deposition (FCVD), atomic layer deposition (ALD), and plasma enhanced atomic layer deposition (PEALD) in the manufacture of a semiconductor device. In other embodiments, the bisaminoalkoxysilanes precursors can be used in a liquid-based deposition or film formation method such as, but not limited to, spin-on, dip coat, aerosol, ink jet, screen printing or spray application. The selection of a precursor material for deposition depends upon the desired resultant dielectric material or film. For example, a precursor material may be chosen for its content of chemical elements, its stoichiometric ratio of chemical elements, and/or the resultant silicon-containing film or coating that is formed under the aforementioned deposition processes. The precursor material may also be chosen for one or more of the following characteristics: cost, non-toxicity, handling characteristics, ability to maintain liquid phase at room temperature, volatility, molecular weight, and/or other considerations. In certain embodiments, the precursors described herein can be delivered to the reactor system by any number of means, preferably using a pressurizable stainless steel vessel fitted with the proper valves and fittings, to allow the delivery of the liquid phase precursor to the deposition chamber or reactor.

It is believed that the bisaminoalkoxysilane precursors described herein may provide better reactivity towards substrate surface during chemical vapor deposition or atomic layer deposition because the precursors have at least one or more of the bonds, Si—N, Si—O, optionally Si—H, and optionally Si—NH, which allow them to chemically react on substrate surfaces during a vapor deposition process. It is believed that the bisaminoalkoxysilane precursors described herein may provide better reactivity towards the substrate surface during chemical vapor deposition, particularly cyclic CVD deposition, or ALD, to form a Si—N—Si linkage or a Si—O—Si linkage due to these bonds. In addition to the foregoing advantages, in certain embodiments such as for depositing a silicon oxide or silicon nitride film using a cyclic CVD, an ALD, or PEALD deposition method, the bisaminoalkoxysilane precursor described herein may be able to deposit high density materials at relatively low deposition temperatures, e.g., at 500° C. or less, at 400° C. or less, or at 300° C. or less. In other embodiments, the precursors described herein can be used, for example, in higher temperature deposition at temperatures ranging from about 500° C. to about 800° C.

Without being bound by theory, it is believed that the compounds described herein overcome the problems associated with other precursors in the prior art by having substituents or ligands with varying relative reactivity. In this connection, the compounds contain silicon-amine substituent groups which are highly reactive and prone to react with a protic reagent such as, without limitation, water in a rapid fashion. This feature allows the precursor to rapidly deposit a flowable film under capillary co-condensation conditions between the precursor, protic reagent, and optional co-solvent. In order to prevent the rapid reaction from causing premature solidification, one can limit the number of highly reactive substituent groups to no more than two per silicon atom, meaning that a three-dimensional networked polymer, which will quickly solidify, cannot form until the remaining, more slowly reactive substituent groups are reacted. An example of this is shown in the following Scheme A wherein the compound having Formula I contains $R^1$=methyl (Me), $R^2$=$R^4$=hydrogen, $R^3$=$R^5$=tert-butyl (But), $R^6$=Me, n=an integer from 3 to 1000, and m=an integer from 4 to 1,000. As Scheme A shows, the tert-butyl amino susbstituent group reacts quickly, or within seconds of contact with water, whereas the methyl hydroxyl substituent group reacts relatively slowly, compared to the tert-butyl amino substituent group, or within minutes to hours of contact with water.

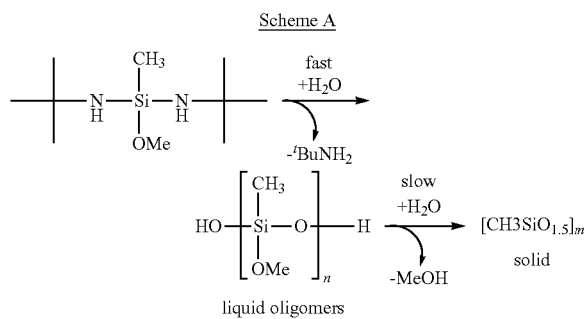

Scheme A

In one embodiment, described herein are deposition processes using bisaminoalkoxysilane compounds having the following Formula I:

$$R^1Si(NR^2R^3)(NR^4R^5)OR^6 \quad\quad I$$

where $R^1$ is selected from a hydrogen atom, a $C_1$ to $C_{10}$ linear alkyl group, a $C_3$ to $C_{10}$ branched alkyl group, a $C_3$ to $C_{10}$ cyclic alkyl group, a $C_3$ to $C_{10}$ alkenyl group, a $C_3$ to $C_{10}$ alkynyl group, a $C_4$ to $C_{10}$ aromatic hydrocarbon group; $R^2$, $R^3$, $R^4$, and $R^5$ are each independently selected from a hydrogen atom, a $C_4$ to $C_{10}$ branched alkyl group, a $C_3$ to $C_{10}$ cyclic alkyl group, a $C_3$ to $C_{10}$ alkenyl group, a $C_3$ to $C_{10}$ alkynyl group, and a $C_4$ to $C_{10}$ aromatic hydrocarbon group; $R^6$ is selected from a $C_1$ to $C_{10}$ linear alkyl group, a $C_3$ to $C_{10}$ branched alkyl group, a $C_3$ to $C_{10}$ cyclic alkyl group, a $C_3$ to $C_{10}$ alkenyl group, a $C_2$ to $C_{10}$ alkynyl group, and a $C_4$ to $C_{10}$ aromatic hydrocarbon group; and optionally wherein $R^2$ and $R^3$, $R^4$ and $R^5$, or both in Formula I can be linked together to form a ring; and optionally wherein $R^2$ and $R^4$ in Formula I can be linked together to form a diamino group.

In one particular embodiment of Formula I, $R^2$ and $R^4$ are both hydrogen atoms and $R^3$ and $R^5$ are independently selected from a 04 to $C_{10}$ branched alkyl group, such as a tert-butyl or tert-pentyl group. Without being bound by any particular theory, it is believed that steric hindrance of the branched alkyl group provides better thermal stability. The term "stable" as used herein means that the precursor described herein does not change 0.5 weight (wt) % or greater, 1 wt % or greater, 2 wt % or greater, 5 wt % or greater, or 10 wt % or greater from its initial composition after being stored for a time period of six (6) months or greater, one (1) year or greater, two (2) years or greater or such other time period which is indicative of being shelf stable. For example, the concentration of the precursor should not compositionally change by more than 10% of its initial percentage based on gas chromatography (GC) or other analytical techniques after storage for 1 year in order to be considered stable as described herein. Good thermal and compositional stability of the precursor is important to ensure consistent precursor delivery to a vapor deposition chamber and consistent vapor deposition parameters. In addition, good thermal stability also reduces the chance for substituent or ligand exchange during storage and handling.

In Formula I and throughout the description, the term "linear alkyl" denotes a linear functional group having from 1 to 10 or 1 to 4 carbon atoms. Exemplary linear alkyl groups include, but are not limited to, methyl, ethyl, n-propyl, n-butyl, n-pentyl, and hexyl groups. In Formula I and throughout the description, the term "branched alkyl" denotes a branched functional group having from 3 to 10 or 4 to 6 carbon atoms. Exemplary alkyl groups include, but are not limited to, isopropyl, isobutyl, sec-butyl, tert-butyl, iso-pentyl, tert-pentyl, and isohexyl. In certain embodiments, the alkyl group may have one or more functional groups such as, but not limited to, an alkoxy group, a dialkylamino group or combinations thereof, attached thereto. In other embodiments, the alkyl group does not have one or more functional groups attached thereto.

In Formula I and throughout the description, the term "cyclic alkyl" denotes a cyclic functional group having from 3 to 10 or from 4 to 10 carbon atoms. Exemplary cyclic alkyl groups include, but are not limited to, cyclobutyl, cyclopentyl, cyclohexyl, and cyclooctyl groups.

In Formula I and throughout the description, the term "aromatic hydrocarbon" denotes an aromatic cyclic functional group having from 4 to 10 carbon atoms. Exemplary aryl groups include, but are not limited to, phenyl, benzyl, chlorobenzyl, tolyl, and o-xylyl. In certain embodiments, the aromatic hydrocarbon group has one or more functional groups.

In Formula I and throughout the description, the term "alkenyl group" denotes a group which has one or more carbon-carbon double bonds and has from 3 to 10 or from 2 to 6 carbon atoms. Exemplary alkenyl groups include, but are not limited to, vinyl or allyl groups In Formula I and throughout the description, the term "alkynyl group" denotes a group which has one or more carbon-carbon triple bonds and has from 3 to 10 or from 2 to 6 carbon atoms.

In Formula I and throughout the description, the term "alkoxy" denotes an alkyl group which has is linked to an oxygen atom (e.g., R—O) and may have from 1 to 12, or from 1 to 6 carbon atoms. Exemplary alkoxy groups include, but are not limited to, methoxy (—OCH$_3$), ethoxy(—OCH$_2$CH$_3$), n-propoxy (—OCH$_2$CH$_2$CH$_3$), and iso-propoxy (—OCHMe$_2$).

In certain embodiments, one or more of the alkyl group, alkenyl group, alkynyl group, alkoxy group, and/or aryl group in Formula I may be substituted or have one or more atoms or group of atoms substituted in place of, for example, a hydrogen atom. Exemplary substituents include, but are not limited to, oxygen, sulfur, halogen atoms (e.g., F, Cl, I, or Br), nitrogen, and phosphorous. In one particular embodiment, the alkyl group in Formula I may comprise oxygen or nitrogen. In other embodiments, one or more of the alkyl group, alkenyl group, alkynyl group, alkoxy group, and/or aryl in Formula I may be unsubstituted.

Examples of the bisaminoalkoxysilane of Formula I described herein include, but are not limited to, bis(tert-butylamino)methoxymethylsilane, bis(tert-butylamino) ethoxymethylsilane, bis(cis-2,6-dimethylpiperidino) methoxymethylsilane, and bis(cis-2,6-dimethylpiperidino) ethoxymethylsilane.

In certain embodiments of the invention described herein, the bisaminoalkoxysilane precursor having the above Formula I can be combined with one or more silicon-containing precursors selected from the group consisting of dialkylaminosilanes, alkoxysilanes, dialkylaminoalkylsilanes, and alkoxyalkylsilanes to provide a composition for depositing a silicon-containing film. In these embodiments, the composition comprises an bisaminoalkoxysilane having Formula I and a silicon-containing precursor. Examples of silicon-containing precursors for these compositions include, but not limited to, bis(tert-butylamino)silane (BTBAS), tris(dimethylamino)silane (TRDMAS), tetraethoxysilane (TEOS), triethoxysilane (TES), di-tert-butoxysilane (DTBOS), di-tert-pentoxysilane (DTPOS), methyltriethoxysilane (MTES), tetramethoxysilane (TMOS), trimethoxysilane (TMOS), methyltrimethoxysilane (MTMOS), di-tert-butoxymethylsilane, di-tert-butoxyethylsilane, di-tert-pentoxymethylsilane, and di-tert-pentoxyethylsilane.

Examples of compositions comprising silicon-containing precursor and a bisaminoalkoxysilane of Formula I include, but are not limited to, tetraethoxysilane (TEOS) and diethoxy(tert-butylamino)silane, tetraethoxysilane (TEOS) and diethoxy(tert-pentylamino)silane, tetraethoxysilane (TEOS) and diethoxy(iso-propoxyamino)silane, triethoxysilane (TES) and diethoxy(tert-butylamino)silane, triethoxysilane (TES) and diethoxy(tert-pentylamino)silane, triethoxysilane (TES) and diethoxy(iso-propoxyamino)silane, di-tert-butoxysilane (DTBOS) and di-tert-butoxy(methylamino)silane, di-tert-butoxysilane (DTBOS) and di-tert-butoxy(ethylamino)silane, di-tert-butoxysilane (DTBOS) and di-tert-butoxy(iso-propylamino)silane, di-tert-butoxysilane (DTBOS) and di-tert-butoxy(n-butylamino)silane, di-tert-butoxysilane (DTBOS) and di-tert-butoxy(sec-butylamino) silane, di-tert-butoxysilane (DTBOS) and di-tert-butoxy (iso-butylamino)silane, di-tert-butoxysilane (DTBOS) and di-tert-butoxy(tert-butylamino)silane, di-tert-pentoxysilane (DTPOS) and di-tert-pentoxy(methylamino)silane, di-tert-pentoxysilane (DTPOS) and di-tert-pentoxy(ethylamino)silane, di-tert-pentoxysilane (DTPOS) and di-tert-pentoxy (iso-propylamino)silane, di-tert-pentoxysilane (DTPOS) and di-tert-pentoxy(n-butylamino)silane, di-tert-pentoxysilane (DTPOS) and di-tert-pentoxy(sec-butylamino)silane, di-tert-pentoxysilane (DTPOS) and di-tert-pentoxy(iso-butylamino)silane, di-tert-pentoxysilane (DTPOS) and di-tert-pentoxy(tert-butylamino)silane. In one particular embodiment, the composition is used to deposit a silicon oxide film by flowable chemical vapor deposition wherein the bisaminoalkoxysilane having Formula I acts as a catalyst. In this or other embodiments, the silicon-containing precursor is selected to be compatible with the bisaminoalkoxysilane by having, for example, the same alkoxy substituent.

As previously mentioned, the deposition method used to form the silicon-containing films or coatings are deposition processes. Examples of suitable deposition processes for the method disclosed herein include, but are not limited to, cyclic CVD (CCVD), thermal chemical vapor deposition, plasma enhanced chemical vapor deposition (PECVD), high density PECVD, photon assisted CVD, plasma-photon assisted (PPECVD), cryogenic chemical vapor deposition, chemical assisted vapor deposition, hot-filament chemical vapor deposition, CVD of a liquid polymer precursor, and low energy CVD (LECVD), and flowable chemical vapor deposition (FCVD).

In one particular embodiment, such as for depositing a silicon oxide using typical FCVD processes, the bisaminoalkoxysilane precursor described herein may be used in combination with other silicon-containing precursors such as those compositions described herein as a catalyst due to release of organoamine as an in situ catalyst at relatively low deposition temperatures, e.g., at 100° C. or less, 50° C. or less, 20° C. or less, even 0° C. or lower.

As used herein, the term "chemical vapor deposition processes" refers to any process wherein a substrate is exposed to one or more volatile precursors, which react and/or decompose on the substrate surface to produce the desired deposition.

As used herein, the term "atomic layer deposition process" refers to a self-limiting (e.g., the amount of film material deposited in each reaction cycle is constant), sequential surface chemistry that deposits films of materials onto substrates of varying compositions. In one embodiment, the film is deposited via an ALD process by exposing the substrate surface alternatively to the one or more the silicon-containing precursor, oxygen source, nitrogen-containing source, or other precursor or reagent. Film growth proceeds by self-limiting control of surface reaction, the pulse length of each precursor or reagent, and the deposition temperature. However, once the surface of the substrate is saturated, the film growth ceases.

Although the precursors, reagents and sources used herein may be sometimes described as "gaseous", it is understood that the precursors can be either liquid or solid which are transported with or without an inert gas into the reactor via direct vaporization, bubbling or sublimation. In some case, the vaporized precursors can pass through a plasma generator.

The term "reactor" as used herein, includes without limitation, reaction chamber or deposition chamber.

Depending upon the deposition method, in certain embodiments, bisaminoalkoxysilane precursors with Formula I, other silicon-containing precursors may be introduced into the reactor at a predetermined molar volume, or from about 0.1 to about 1000 micromoles. In this or other embodiments, the bisaminoalkoxysilane precursor may be introduced into the reactor for a predetermined time period. In certain embodiments, the time period ranges from about 0.001 to about 500 seconds.

In certain embodiments, the silicon-containing films deposited using the methods described herein are formed in the presence of oxygen using an oxygen source, reagent or precursor comprising oxygen.

An oxygen source may be introduced into the reactor in the form of at least one oxygen source and/or may be present incidentally in the other precursors used in the deposition process.

Suitable oxygen source gases may include, for example, water ($H_2O$) (e.g., deionized water, purifier water, and/or distilled water, a mixture containing water and other organic liquid), oxygen ($O_2$), oxygen plasma, ozone ($O_3$), NO, $NO_2$, carbon monoxide (CO), hydrogen peroxide, a composition comprising hydrogen and oxygen, carbon dioxide ($CO_2$) and combinations thereof. The organic liquid in the mixture can be selected from hydrocarbon, aromatic hydrocarbon, ether, amine, ketone, ester, alcohols, organic acid, diols, acetylenic alcohols and organic amide.

In certain embodiments, the oxygen source comprises an oxygen source gas that is introduced into the reactor at a flow rate ranging from about 1 to about 2000 square cubic centimeters (sccm) or from about 1 to about 1000 sccm. The oxygen source can be introduced for a time that ranges from about 0.1 to about 100 seconds.

In one particular embodiment, the oxygen source comprises water having a temperature of 10° C. or greater.

In embodiments wherein the film is deposited by an ALD or a cyclic CVD process, the precursor pulse can have a pulse duration that is greater than 0.01 seconds, and the oxygen source can have a pulse duration that is less than 0.01 seconds, while the water pulse duration can have a pulse duration that is less than 0.01 seconds.

In yet another embodiment, the purge duration between the pulses that can be as low as 0 seconds or is continuously pulsed without a purge in-between. The oxygen source or reagent is provided in a molecular amount less than a 1:1 ratio to the silicon precursor, so that at least some carbon is retained in the as deposited silicon-containing film.

In certain embodiments, oxygen source is continuously flowing into the reactor while precursor pulse and plasma are introduced in sequence. The precursor pulse can have a pulse duration greater than 0.01 seconds while the plasma duration can range between 0.01 seconds to 100 seconds.

In certain embodiments, the silicon-containing films comprise silicon and nitrogen. In these embodiments, the silicon-containing films deposited using the methods described herein are formed in the presence of nitrogen-containing source. An nitrogen-containing source may be introduced into the reactor in the form of at least one nitrogen source and/or may be present incidentally in the other precursors used in the deposition process.

Suitable nitrogen-containing source gases may include, for example, ammonia, hydrazine, monoalkylhydrazine, symmetrical or unsymmetrical dialkylhydrazine, nitrogen, NO, $N_2O$, $NO_2$, nitrogen/hydrogen, ammonia plasma, nitrogen plasma, ammonia/nitrogen plasma, nitrogen/hydrogen plasma, an organoamine plasma, and mixture thereof. In embodiments wherein an organoamine plasma is used as a nitrogen-containing source, exemplary organic amine plasmas included, are not limited to, diethylamine plasma, dimethylamine plasma, trimethyl plasma, trimethylamine plasma, ethylenediamine plasma, and an alkoxyamine such as ethanolamine plasma.

In certain embodiments, the nitrogen-containing source comprises an ammonia plasma or a plasma source gas comprising hydrogen and nitrogen that is introduced into the reactor at a flow rate ranging from about 1 to about 2000 square cubic centimeters (sccm) or from about 1 to about 1000 sccm.

The nitrogen-containing source can be introduced for a time that ranges from about 0.1 to about 100 seconds. In embodiments wherein the film is deposited by an ALD or a cyclic CVD process, the precursor pulse can have a pulse duration that is greater than 0.01 seconds, and the nitrogen-containing source can have a pulse duration that is less than 0.01 seconds, while the water pulse duration can have a pulse duration that is less than 0.01 seconds. In yet another embodiment, the purge duration between the pulses that can be as low as 0 seconds or is continuously pulsed without a purge in-between.

The deposition methods disclosed herein may involve one or more purge gases. The purge gas, which is used to purge away unconsumed reactants and/or reaction byproducts, is an inert gas that does not react with the precursors. Exemplary purge gases include, but are not limited to, argon (Ar), nitrogen ($N_2$), helium (He), neon, hydrogen ($H_2$), and mixtures thereof. In certain embodiments, a purge gas such as Ar is supplied into the reactor at a flow rate ranging from 10 to about 2000 sccm for about 0.1 to 1000 seconds, thereby purging the unreacted material and any byproduct that may remain in the reactor.

The respective step of supplying the precursors, oxygen source, the nitrogen-containing source, and/or other precursors, source gases, and/or reagents may be performed by changing the time for supplying them to change the stoichiometric composition of the resulting film.

Energy is applied to the at least one of the precursor, nitrogen-containing source, reducing agent, other precursors or combination thereof to induce reaction and to form the film or coating on the substrate. Such energy can be provided by, but not limited to, thermal, plasma, pulsed plasma, helicon plasma, high density plasma, inductively coupled plasma, X-ray, e-beam, photon, remote plasma methods, and combinations thereof.

In certain embodiments, a secondary RF frequency source can be used to modify the plasma characteristics at the substrate surface. In embodiments wherein the deposition involves plasma, the plasma-generated process may comprise a direct plasma-generated process in which plasma is directly generated in the reactor, or alternatively a remote plasma-generated process in which plasma is generated outside of the reactor and supplied into the reactor.

The bisaminoalkoxysilane precursors and/or other silicon-containing precursors may be delivered to the reaction chamber, such as a CVD or ALD reactor, in a variety of ways. In one embodiment, a liquid delivery system may be utilized. In an alternative embodiment, a combined liquid delivery and flash vaporization process unit may be employed, such as, for example, the turbo vaporizer manufactured by MSP Corporation of Shoreview, Minn., to enable low volatility materials to be volumetrically delivered, which leads to reproducible transport and deposition without thermal decomposition of the precursor. In liquid delivery formulations, the precursors described herein may be delivered in neat liquid form, or alternatively, may be employed in solvent formulations or compositions comprising same. Thus, in certain embodiments the precursor formulations may include solvent component(s) of suitable character as may be desirable and advantageous in a given end use application to form a film on a substrate.

In this or other embodiments, it is understood that the steps of the methods described herein may be performed in a variety of orders, may be performed sequentially or concurrently (e.g., during at least a portion of another step), and any combination thereof. The respective step of supplying the precursors and the nitrogen-containing source gases may be performed by varying the duration of the time for supplying them to change the stoichiometric composition of the resulting silicon-containing film.

In another embodiment of the method disclosed herein, silicon-containing films are formed using an ALD deposition method that comprises the steps of:

providing a substrate in an ALD reactor;
introducing into the ALD reactor at least one precursor comprising an bisaminoalkoxysilane compounds having a Formula I:

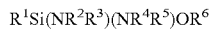

$$R^1Si(NR^2R^3)(NR^4R^5)OR^6 \quad\quad I$$

where $R^1$ is selected from a hydrogen atom, a $C_1$ to $C_{10}$ linear alkyl group, a $C_3$ to $C_{10}$ branched alkyl group, a $C_3$ to $C_{10}$ cyclic alkyl group, a $C_3$ to $C_{10}$ alkenyl group, a $C_3$ to $C_{10}$ alkynyl group, a $C_4$ to $C_{10}$ aromatic hydrocarbon group; $R^2$, $R^3$, $R^4$, and $R^5$ are each independently selected from a hydrogen atom, a $C_4$ to $C_{10}$ branched alkyl group, a $C_3$ to $C_{10}$ cyclic alkyl group, a $C_3$ to $C_{10}$ alkenyl group, a $C_3$ to $C_{10}$ alkynyl group, and a $C_4$ to $C_{10}$ aromatic hydrocarbon group; $R^6$ is selected from a $C_1$ to $C_{10}$ linear alkyl group, a $C_3$ to $C_{10}$ branched alkyl group, a $C_3$ to $C_{10}$ cyclic alkyl group, a $C_3$ to $C_{10}$ alkenyl group, a $C_2$ to $C_{10}$ alkynyl group, and a $C_4$ to $C_{10}$ aromatic hydrocarbon group; and optionally wherein $R^2$ and $R^3$, $R^4$ and $R^5$, or both in Formula I can be linked together to form a ring; and optionally wherein $R^2$ and $R^4$ in Formula I can be linked together to form a diamino group;

chemisorbing the at least one bisaminoalkoxysilane precursor onto a substrate;
purging away the unreacted at least one bisaminoalkoxysilane precursor using a purge gas;
providing a nitrogen-containing source to the at least one bisaminoalkoxysilane precursor onto the heated substrate to react with the sorbed at least one bisaminoalkoxysilane precursor; and
optionally purging away any unreacted nitrogen-containing source.

In another embodiment of the method disclosed herein, the silicon-containing films are formed using an ALD deposition method that comprises the steps of:

providing a substrate in a reactor;
introducing into the reactor an at least one precursor comprising an bisaminoalkoxysilane compounds having a Formula (I):

$$R^1Si(NR^2R^3)(NR^4R^5)OR^6 \quad\quad I$$

where $R^1$ is selected from a hydrogen atom, a $C_1$ to $C_{10}$ linear alkyl group, a $C_3$ to $C_{10}$ branched alkyl group, a $C_3$ to $C_{10}$ cyclic alkyl group, a $C_3$ to $C_{10}$ alkenyl group, a $C_3$ to $C_{10}$ alkynyl group, a $C_4$ to $C_{10}$ aromatic hydrocarbon group; $R^2$, $R^3$, $R^4$, and $R^5$ are each independently selected from a hydrogen atom, a $C_4$ to $C_{10}$ branched alkyl group, a $C_3$ to $C_{10}$ cyclic alkyl group, a $C_3$ to $C_{10}$ alkenyl group, a $C_3$ to $C_{10}$ alkynyl group, and a $C_4$ to $C_{10}$ aromatic hydrocarbon group; $R^6$ is selected from a $C_1$ to $C_{10}$ linear alkyl group, a $C_3$ to $C_{10}$ branched alkyl group, a $C_3$ to $C_{10}$ cyclic alkyl group, a $C_3$ to $C_{10}$ alkenyl group, a $C_2$ to $C_{10}$ alkynyl group, and a $C_4$ to $C_{10}$ aromatic hydrocarbon group; and optionally wherein $R^2$ and $R^3$, $R^4$ and $R^5$, or both in Formula I can be linked together to form a ring; and optionally wherein $R^2$ and $R^4$ in Formula I can be linked together to form a diamino group;

chemisorbing the at least one bisaminoalkoxysilane precursor onto a substrate;
purging away the unreacted at least one bisaminoalkoxysilane precursor using a purge gas;
providing an oxygen source to the at least one bisaminoalkoxysilane precursor onto the heated substrate to react with the sorbed at least one bisaminoalkoxysilane precursor; and optionally purging away any unreacted oxygen source.

The above steps define one cycle for the method described herein; and the cycle can be repeated until the desired thickness of a silicon-containing film is obtained. In this or other embodiments, it is understood that the steps of the methods described herein may be performed in a variety of orders, may be performed sequentially or concurrently (e.g., during at least a portion of another step), and any combination thereof. The respective step of supplying the precursors and oxygen source may be performed by varying the duration of the time for supplying them to change the stoichiometric composition of the resulting silicon-containing film, although always using oxygen in less than a stoichiometric amount relative to the available silicon. For multi-component silicon-containing films, other precursors such as silicon-containing precursors, nitrogen-containing precursors, reducing agents, or other reagents can be alternately introduced into the reactor chamber.

In a further embodiment of the method described herein, the silicon and oxide containing film is deposited using a thermal CVD process. In this embodiment, the method comprises:

placing one or more substrates into a reactor which is heated to a temperature ranging from ambient temperature to about 700° C. and maintained at a pressure of 10 Torr or less;
introducing at least one precursor comprising a bisaminoalkoxysilane compounds having a Formula I:

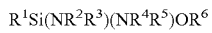

$$R^1Si(NR^2R^3)(NR^4R^5)OR^6 \quad\quad I$$

where $R^1$ is selected from a hydrogen atom, a $C_1$ to $C_{10}$ linear alkyl group, a $C_3$ to $C_{10}$ branched alkyl group, a $C_3$ to $C_{10}$ cyclic alkyl group, a $C_3$ to $C_{10}$ alkenyl group, a $C_3$ to $C_{10}$ alkynyl group, a $C_4$ to $C_{10}$ aromatic hydrocarbon group; $R^2$, $R^3$, $R^4$, and $R^5$ are each independently selected from a hydrogen atom, a $C_4$ to $C_{10}$ branched alkyl group, a $C_3$ to $C_{10}$ cyclic alkyl group, a $C_3$ to $C_{10}$ alkenyl group, a $C_3$ to $C_{10}$ alkynyl group, and a $C_4$ to $C_{10}$ aromatic hydrocarbon group; $R^6$ is selected from a $C_1$ to $C_{10}$ linear alkyl group, a $C_3$ to $C_{10}$ branched alkyl group, a $C_3$ to $C_{10}$ cyclic alkyl group, a $C_3$ to $C_{10}$ alkenyl group, a $C_2$ to $C_{10}$ alkynyl group, and a $C_4$ to $C_{10}$ aromatic hydrocarbon group; and optionally wherein $R^2$ and $R^3$, $R^4$ and $R^5$, or both in Formula I can be linked together to form a ring; and optionally wherein $R^2$ and $R^4$ in Formula I can be linked together to form a diamino group; and

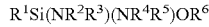

providing an oxygen source into the reactor to at least partially react with the at least one bisaminoalkoxysilane precursor and deposit the film onto the one or more substrates. In certain embodiments of the CVD method, the reactor is maintained at a pressure ranging from 100 mTorr to 10 Torr during the introducing step.

The above steps define one cycle for the method described herein; and the cycle can be repeated until the desired thickness of a silicon-containing film is obtained. In this or other embodiments, it is understood that the steps of the methods described herein may be performed in a variety of orders, may be performed sequentially or concurrently (e.g., during at least a portion of another step), and any combination thereof. The respective step of supplying the precursors and oxygen source may be performed by varying the duration of the time for supplying them to change the stoichiometric composition of the resulting silicon-containing film, although always using oxygen in less than a stoichiometric amount relative to the available silicon. For multi-component silicon-containing films, other precursors such as silicon-containing precursors, nitrogen-containing precursors, oxygen sources, reducing agents, and/or other reagents can be alternately introduced into the reactor chamber.

In a further embodiment of the method described herein, the silicon and nitride containing film is deposited using a thermal CVD process. In this embodiment, the method comprises:

placing one or more substrates into a reactor which is heated to a temperature ranging from ambient temperature to about 700° C. and maintained at a pressure of 10 Torr or less;

introducing at least one precursor comprising a bisaminoalkoxysilane compound having a Formula I:

$$R^1Si(NR^2R^3)(NR^4R^5)OR^6 \qquad I$$

where $R^1$ is selected from a hydrogen atom, a $C_1$ to $C_{10}$ linear alkyl group, a $C_3$ to $C_{10}$ branched alkyl group, a $C_3$ to $C_{10}$ cyclic alkyl group, a $C_3$ to $C_{10}$ alkenyl group, a $C_3$ to $C_{10}$ alkynyl group, a $C_4$ to $C_{10}$ aromatic hydrocarbon group; $R^2$, $R^3$, $R^4$, and $R^5$ are each independently selected from a hydrogen atom, a $C_4$ to $C_{10}$ branched alkyl group, a $C_3$ to $C_{10}$ cyclic alkyl group, a $C_3$ to $C_{10}$ alkenyl group, a $C_3$ to $C_{10}$ alkynyl group, and a $C_4$ to $C_{10}$ aromatic hydrocarbon group; $R^6$ is selected from a $C_1$ to $C_{10}$ linear alkyl group, a $C_3$ to $C_{10}$ branched alkyl group, a $C_3$ to $C_{10}$ cyclic alkyl group, a $C_3$ to $C_{10}$ alkenyl group, a $C_2$ to $C_{10}$ alkynyl group, and a $C_4$ to $C_{10}$ aromatic hydrocarbon group; and optionally wherein $R^2$ and $R^3$, $R^4$ and $R^5$, or both in Formula I can be linked together to form a ring; and optionally wherein $R^2$ and $R^4$ in Formula I can be linked together to form a diamino group; and providing a nitrogen-containing source into the reactor to at least partially react with the at least one bisaminoalkoxysilane precursor and deposit a silicon-containing film onto the one or more substrates. In certain embodiments of the CVD method, the reactor is maintained at a pressure ranging from 100 mTorr to 10 Torr during the introducing step.

As previously mentioned, the process described herein can be used to deposit a film using more than one precursor such as the bisaminoalkoxysilane compound having Formula I described herein with an additional precursor such as another silicon-containing precursor such as those described herein. In these embodiments, the one or more precursors are described as a first precursor, a second precursor, a third precursor, etc. depending upon the number of different precursors used. The process can be used, for example, in a cyclic chemical vapor deposition or an atomic layer deposition. In these or other embodiments, the precursors can be introduced in a variety of ways (e.g., a. introduce first precursor; b. purge; c. introduce second precursor; d. purge; e. introduce third precursor; f. purge, etc., or, alternatively, a. introduce first precursor; b. purge; c. introduce second precursor; d. purge; e. introduce second precursor; etc.) In one particular embodiment, there is provided a process to deposit a silicon-containing film comprising the following steps:

a. Contacting vapors generated from a first precursor with a heated substrate to chemically sorb the first precursor on the heated substrate;
b. Purging away any unsorbed precursors;
c. Introducing an oxygen source on the heated substrate to react with the sorbed first precursor;
d. Purging away any unreacted oxygen source;
e. Contacting vapors generated from a second precursor which is different from the first precursor with a heated substrate to chemically sorb the second precursor on the heated substrate;
f. Purging away any unsorbed precursors;
g. Introducing an oxygen source on the heated substrate to react with the sorbed first and second precursors; and
h. Purging away any unreacted oxygen source wherein steps a. through h. are repeated until a desired thickness has been reached.

In a yet another embodiment of the process described herein, there is provided a method of depositing a silicon-containing film comprising the following steps:

a. Contacting vapors generated from a first precursor with a heated substrate to chemically sorb the first precursors on the heated substrate;
b. Purging away any unsorbed first precursors;
c. Introducing a nitrogen source on the heated substrate to react with the sorbed first precursor;
d. Purging away any unreacted nitrogen source;
e. Contacting vapors generated from a second precursor which is different from the first with a heated substrate to chemically sorb the second precursor on the heated substrate;
f. Purging away any unsorbed second precursors;
g. Introducing a nitrogen source on the heated substrate to react with the sorbed second precursor; and
h. Purging away any unreacted nitrogen source wherein steps a. through h. are repeated until a desired thickness of film has been reached.

In another embodiment, there is described a method for depositing a silicon-containing film in a flowable chemical vapor deposition process wherein the substrate has at least one surface feature. The term "surface feature" as used herein means a feature such as, without limitation, pore, trench, well, step, gap, via, and combination thereof.

In one particular embodiment, the flowable chemical vapor deposition process comprises the steps of:

placing a substrate having a surface feature into a reactor which are maintained at a temperature ranging from −20° C. to about 400° C.;

introducing into the reactor at least one precursor comprising a bisaminoalkoxysilane compounds having a Formula I:

$$R^1Si(NR^2R^3)(NR^4R^5)OR^6 \qquad I$$

where $R^1$ is selected from a hydrogen atom, a $C_1$ to $C_{10}$ linear alkyl group, a $C_3$ to $C_{10}$ branched alkyl group, a $C_3$ to $C_{10}$ cyclic alkyl group, a $C_3$ to $C_{10}$ alkenyl group, a $C_3$ to $C_{10}$ alkynyl group, a $C_4$ to $C_{10}$ aromatic hydrocarbon group; $R^2$, $R^3$, $R^4$, and $R^5$ are each independently selected from a hydrogen atom, a $C_4$ to $C_{10}$ branched alkyl group, a $C_3$ to $C_{10}$ cyclic alkyl group, a $C_3$ to $C_{10}$ alkenyl group, a $C_3$ to $C_{10}$ alkynyl group, and a $C_4$ to $C_{10}$ aromatic hydrocarbon group; $R^6$ is selected from a $C_1$ to $C_{10}$ linear alkyl group, a $C_3$ to $C_{10}$ branched alkyl group, a $C_3$ to $C_{10}$ cyclic alkyl group, a $C_3$ to $C_{10}$ alkenyl group, a $C_2$ to $C_{10}$ alkynyl group, and a $C_4$ to $C_{10}$ aromatic hydrocarbon group; and optionally wherein $R^2$ and $R^3$, $R^4$ and $R^5$, or both in Formula I can be linked together to form a ring; and optionally wherein $R^2$ and $R^4$ in Formula I can be linked together to form a diamino group and a nitrogen source wherein the at least one compound reacts with the nitrogen source to form a nitride containing film on at least a portion of the surface feature; and treating the substrate with an oxygen source at one or more temperatures ranging from about 100° C. to about 1000° C. to form the film on at least a portion of the surface feature. In an alternative embodiment, the film may be exposed to an oxygen source while being exposed to UV irradiation at temperatures ranging from about 100° C. to about 1000° C. The process steps can be repeated until the surface features are filled with the high quality silicon oxide film.

In a further embodiment of the method described herein, the film is deposited using a flowable CVD process. In this embodiment, the method comprises:

placing one or more substrates comprising a surface feature into a reactor which is heated to a temperature ranging from −20° C. to about 400° C. and maintained at a pressure of 100 Torr or less;

introducing at least one precursor comprising a bisaminoalkoxysilane compound having Formula I:

$$R^1Si(NR^2R^3)(NR^4R^5)OR^6 \qquad \text{I}$$

where $R^1$ is selected from a hydrogen atom, a $C_1$ to $C_{10}$ linear alkyl group, a $C_3$ to $C_{10}$ branched alkyl group, a $C_3$ to $C_{10}$ cyclic alkyl group, a $C_3$ to $C_{10}$ alkenyl group, a $C_3$ to $C_{10}$ alkynyl group, a $C_4$ to $C_{10}$ aromatic hydrocarbon group; $R^2$, $R^3$, $R^4$, and $R^5$ are each independently selected from a hydrogen atom, a $C_4$ to $C_{10}$ branched alkyl group, a $C_3$ to $C_{10}$ cyclic alkyl group, a $C_3$ to $C_{10}$ alkenyl group, a $C_3$ to $C_{10}$ alkynyl group, and a $C_4$ to $C_{10}$ aromatic hydrocarbon group; $R^6$ is selected from a $C_1$ to $C_{10}$ linear alkyl group, a $C_3$ to $C_{10}$ branched alkyl group, a $C_3$ to $C_{10}$ cyclic alkyl group, a $C_3$ to $C_{10}$ alkenyl group, a $C_2$ to $C_{10}$ alkynyl group, and a $C_4$ to $C_{10}$ aromatic hydrocarbon group; and optionally wherein $R^2$ and $R^3$, $R^4$ and $R^5$, or both in Formula I can be linked together to form a ring; and optionally wherein $R^2$ and $R^4$ in Formula I can be linked together to form a diamino group;

providing an oxygen source into the reactor to react with the at least one compound to form a film and cover at least a portion of the surface feature;

annealing the film at one or more temperatures ranging from about 100° C. to about 1000° C. to allow the silicon-containing film to coat at least a portion of the surface feature. The oxygen source of this embodiment is selected from the group consisting of water vapors, water plasma, ozone, oxygen, oxygen plasma, oxygen/helium plasma, oxygen/argon plasma, nitrogen oxides plasma, carbon dioxide plasma, hydrogen peroxide, organic peroxides, and mixtures thereof. The process can be repeated until the surface features are filled with the silicon-containing film. When water vapors are employed as oxygen source in this embodiment, the substrate temperatures are preferably between −20 and 100° C., most preferably between −10 and 80° C.

In one particular embodiment, the method for depositing a film selected from a silicon oxynitride and a carbon-doped silicon oxynitride in a flowable chemical vapor deposition process which comprises:

placing a substrate having a surface feature into a reactor which are maintained at a temperature ranging from −20° C. to about 400° C.;

introducing into the reactor at least one precursor comprising a bisaminoalkoxysilane compound having Formula I:

$$R^1Si(NR^2R^3)(NR^4R^5)OR^6 \qquad \text{I}$$

where $R^1$ is selected from a hydrogen atom, a $C_1$ to $C_{10}$ linear alkyl group, a $C_3$ to $C_{10}$ branched alkyl group, a $C_3$ to $C_{10}$ cyclic alkyl group, a $C_3$ to $C_{10}$ alkenyl group, a $C_3$ to $C_{10}$ alkynyl group, a $C_4$ to $C_{10}$ aromatic hydrocarbon group; $R^2$, $R^3$, $R^4$, and $R^5$ are each independently selected from a hydrogen atom, a $C_4$ to $C_{10}$ branched alkyl group, a $C_3$ to $C_{10}$ cyclic alkyl group, a $C_3$ to $C_{10}$ alkenyl group, a $C_3$ to $C_{10}$ alkynyl group, and a $C_4$ to $C_{10}$ aromatic hydrocarbon group; $R^6$ is selected from a $C_1$ to $C_{10}$ linear alkyl group, a $C_3$ to $C_{10}$ branched alkyl group, a $C_3$ to $C_{10}$ cyclic alkyl group, a $C_3$ to $C_{10}$ alkenyl group, a $C_2$ to $C_{10}$ alkynyl group, and a $C_4$ to $C_{10}$ aromatic hydrocarbon group; and optionally wherein $R^2$ and $R^3$, $R^4$ and $R^5$, or both in Formula I can be linked together to form a ring; and optionally wherein $R^2$ and $R^4$ in Formula I can be linked together to form a diamino group and a nitrogen source wherein the at least one compound reacts with the nitrogen source to form a nitride containing film on at least a portion of the surface feature; and treating the substrate with a nitrogen source to form silicon oxynitride or a carbon-doped silicon oxynitride films to cover at least a portion of the surface feature. Optionally, the film may be exposed to UV irradiation at temperatures ranging from about 100° C. to about 1000° C. to densify the resulting films.

In a further embodiment, described herein is a process is deposit silicon-containing films employing cyclic chemical vapor deposition (CCVD) or atomic layer deposition (ALD) techniques such as, but not limited to, plasma enhanced ALD (PEALD) or plasma enhanced CCVD (PECCVD) process. In these embodiments, the deposition temperature may be relatively high, or from about 500 to 800° C., to control the specifications of film properties required in certain semiconductor applications. In one particular embodiment, the process comprises the following steps: contacting vapors generated from a bisaminoalkoxysilane having Formula I or A with a heated substrate to chemically sorb the precursors on the heated substrate; purging away any unsorbed precursors; introducing a reducing agent to reduce the sorbed precursors; and purging away any unreacted reducing agent.

In another embodiment, a vessel for depositing a silicon-containing film comprising one or more bisaminoalkoxysilane precursor compounds having Formula I described herein. In one particular embodiment, the vessel comprises at least one pressurizable vessel (preferably of stainless steel) fitted with the proper valves and fittings to allow the delivery of one or more precursors to the reactor for a CVD or an ALD process. In this or other embodiments, the bisaminoalkoxysilane precursor is provided in a pressurizable vessel comprised of stainless steel and the purity of the precursor is 98% by weight or greater or 99.5% or greater which is suitable for the majority of semiconductor applications. In certain embodiments, such vessels can also have means for mixing the precursors with one or more additional precursor if desired. In these or other embodiments, the contents of the vessel(s) can be premixed with an additional precursor. Alternatively, the bisaminoalkoxysilane precursor and/or other precursor can be maintained in separate vessels or in a single vessel having separation means for maintaining the bisaminoalkoxysilane precursor and other precursor separate during storage.

In one embodiment of the method described herein, a cyclic deposition process such as CCVD, ALD, or PEALD may be employed, wherein at least one bisaminoalkoxysilane precursor having Formula I and optionally a nitrogen-containing source such as, for example, ammonia, hydrazine, monoalkylhydrazine, dialkylhydrazine, nitrogen, nitrogen/hydrogen, ammonia plasma, nitrogen plasma, a plasma comprising nitrogen and hydrogen are employed.

Throughout the description, the term "ALD or ALD-like" refers to a process including, but not limited to, the following processes: a) each reactant including bisaminoalkoxysilane precursor and reactive gas is introduced sequentially into a reactor such as a single wafer ALD reactor, semi-batch ALD reactor, or batch furnace ALD reactor; b) each reactant including bisaminoalkoxysilane precursor and reactive gas is exposed to a substrate by moving or rotating the substrate to different sections of the reactor and each section is separated by inert gas curtain, i.e. spatial ALD reactor or roll to roll ALD reactor.

In certain embodiments, the silicon-containing films are deposited using a flowable chemical vapor deposition (FCVD) process. In one particular embodiment of a FCVD process, bisaminoalkoxysilane precursors described herein react with a protic reagent such as water to form a flowable liquid which can fill at least a portion of a surface feature of a substrate and optionally treating the substrate with at least one treatment selected from the group consisting of thermal annealing, ultraviolet (UV) light exposure, infrared (IR) to provide a solid silicon and oxygen containing film. In another embodiment of the FCVD process, the bisaminoalkoxysilane precursors described herein react with an oxygen source (other than water) to form a flowable liquid which can fill at least a portion of a surface feature on a substrate and optionally treating the substrate with at least one treatment selected from the group consisting of thermal annealing, ultraviolet (UV) light exposure, infrared (IR) to provide a solid silicon and oxygen containing film. In a still further embodiment of the FCVD process described herein, the bisaminoalkoxysilane precursors described herein react with a nitrogen source to form a flowable liquid which can fill at least a portion of a surface feature on a substrate, treating the substrate with at least one treatment selected from the group consisting of thermal annealing, ultraviolet (UV) light exposure, infrared (IR) to provide a solid silicon and nitrogen containing film, and optionally converting the solid silicon and nitrogen containing film into a solid silicon and oxide containing by treating with an oxygen source. The nitrogen-containing source can be selected from the group consisting of ammonia, hydrazine, monoalkylhydrazine, dialkylhydrazine, a plasma comprising nitrogen and hydrogen, ammonia plasma, nitrogen plasma, organic amines including, but not limited to, methylamine, dimethylamine, trimethylamine, ethylamine, diethylamine, trimethylamine, tert-butylamine, ethylenediamine, ethanolamine, organic amine plasma. In yet another embodiment of a FCVD process, the bisaminoalkoxysilane precursors described herein react with a plasma source to form a flowable liquid which can fill at least a portion of a surface feature of a substrate and optionally treating the substrate with at least one treatment selected from the group consisting of thermal annealing, ultraviolet (UV) light exposure, infrared (IR) to provide a solid silicon containing film. The plasma source can be selected from the group consisting of helium plasm, argon plasma, a plasma comprising helium and hydrogen, a plasma comprising argon and hydrogen. When a plasma is applied for FCVD or other deposition processes, the plasma can be generated in situ or remotely. With regard to embodiments using a FCVD deposition process, in one particular embodiment, a remote plasma generator is used as it causes less damage to the structures on the substrate.

As mentioned previously, the method described herein may be used to deposit a silicon-containing film on at least a portion of a substrate. Examples of suitable substrates include but are not limited to, silicon, $SiO_2$, $Si_3N_4$, OSG, FSG, silicon carbide, hydrogenated silicon carbide, silicon nitride, hydrogenated silicon nitride, silicon carbonitride, hydrogenated silicon carbonitride, boronitride, antireflective coatings, photoresists, organic polymers, porous organic and inorganic materials, metals such as copper and aluminum, and diffusion barrier layers such as but not limited to TiN, Ti(C) N, TaN, Ta(C) N, Ta, W, or WN. The films are compatible with a variety of subsequent processing steps such as, for example, chemical mechanical planarization (CMP) and anisotropic etching processes.

The deposited films have applications, which include, but are not limited to, computer chips, optical devices, magnetic information storages, coatings on a supporting material or substrate, microelectromechanical systems (MEMS), nanoelectromechanical systems, thin film transistor (TFT), and liquid crystal displays (LCD).

WORKING EXAMPLES

Example 1: Synthesis of bis (tert-butylamino) ethoxymethylsilane

To a solution of 72.0 g (481.7 mmol) of methyltrichlorosilane in 1.5 L of anhydrous THF chilled to −30° C. was added 140.9 g (1926.7 mmol) of tert-butylamine drop-wise via an addition funnel while maintaining the internal temperature of the reaction at −30° C. The resulting white slurry was stirred with a mechanical stirrer. Tert-butylamine hydrochloride salt was filtered off from the resulting thick slurry, washed with an additional 200 mL of hexanes, and pressed to extract residual product possibly trapped in the salt. In a separate reaction, to a solution of 22.2 g (480.8 mmol) ethanol in 300 mL of anhydrous THF at −30° C. was added 205.0 mL (512.5 mmol) of a solution of 2.5M n-butyllithium in hexanes drop-wise while maintaining the internal temperature at −30° C. After addition of the nBuLi was complete, the reaction mixture turned from clear to a bright yellow suspension. The reaction mixture was then allowed to warm to room temperature and stirred with a magnetic stir bar. After stirring overnight, the lithium ethoxide reaction mixture turned from a bright yellow suspension to a white slurry. The lithium ethoxide reaction was then added in situ via an addition funnel to the filtered reaction mixture from step 1 while maintaining the reaction at <0° C. The addition of the lithium ethoxide was done rather quickly as the reaction was witnessed to not be that exothermic. The resulting white suspension was warmed to room temperature and stirred. After the course of a few hours, the reaction mixture turned from a white suspension, to yellow, to orange. The crude reaction mixture was filtered through a medium frit isolating 25.0 g of a brown solid reminiscent of lithium chloride. The filtrate was an amber orange solution and subjected to rotovap at 100 Torr with an oil bath temperature of 50° C. to remove solvent. Isolated 109.26 g of crude material and purification was done by fractional distillation at 82° C. and 10 Torr. 51.4 g of a clear liquid was isolated at 92.5% assay. Thermogravimetric analysis (TGA)/differential scanning calorimetry (DCS) indicates a boiling point at 205° C. and 2.52% residual. Stability testing showed an average purity increase of 0.38% after heating for 4 days at 80° C. The assay increased from 90.18% to 90.56%.

Example 2: Synthesis of bis(tert-butylamino)methoxymethylsilane

To a solution of 72.0 g (481.7 mmol) of methyltrichlorosilane in 1.5 L of anhydrous THF chilled to −30° C. was added 140.9 g (1926.7 mmol) of tert-butylamine drop-wise via addition funnel while maintaining the internal temperature of the reaction at −30° C. The resulting white slurry was stirred with a mechanical stirrer. Tert-butylamine hydrochloride salt was filtered off from the resulting thick slurry, washed with an additional 200 mL of hexanes, and pressed to extract residual product possibly trapped in the salt. In a separate reaction, to a solution of 15.4 g (481.7 mmol) methanol in 300 mL of anhydrous THF at −30° C. was added 202.3 mL (505.8 mmol) of a solution of 2.5M n-butyllithium in hexanes drop-wise while maintaining the internal temperature at −30° C. After addition of the nBuLi was complete, the reaction mixture was allowed to warm to room temperature and stirred with a magnetic stir bar. After stirring overnight, the lithium methoxide reaction mixture was added in situ via an addition funnel to the filtered reaction mixture from step 1 while maintaining the reaction at <0° C. The resulting white suspension was warmed to room temperature and stirred. A total of 250 mL of THF was added to provide adequate solubility for the reaction to go to completion. Filtration yielded a slightly yellow powder weighting 21.5 g reminiscent of lithium chloride. Solvent was removed from the filtrate by rotovap to isolate 122.45 g of crude material. Purification was carried out by vacuum distillation using a packed column at 75° C. and 10 Torr. A clear liquid was isolated in the amount of 78.7 g. Samples were submitted for stability and TGA/DSC. DSC indicates a boiling point of 186.6° C. Further observations showed an average increase in assay of 0.08% (90.79% to 90.87%) after heating in triplicate for three days at 80° C.

Example 3: Synthesis of bis(tert-butylamino)isopropoxymethylsilane

To a solution of 3.35 g (22.44 mmol) of methyltrichlorosilane in 50 mL of hexanes chilled to −30° C. was added 6.56 g (89.75 mmol) tert-butylamine drop-wise while maintaining the internal temperature of the reaction at −30° C. The resulting white slurry was stirred with a magnetic stir bar. Tert-butylamine hydrochloride, as a white salt, was filtered off from the resulting thick slurry, washed with an additional 20 mL of hexanes, and pressed to extract residual product possibly trapped in the salt. In a separate reaction, to a solution of 1.35 g (22.44 mmol) isopropyl alcohol in 30 mL of anhydrous THF at −30° C. was added 9.0 mL (22.4 mmol) of a solution of 2.5M n-butyllithium in hexanes drop-wise while maintaining the internal temperature at −30° C. After addition of the nBuLi was complete, the reaction mixture was then allowed to warm to room temperature and added in situ to the filtered reaction mixture from step 1. The resulting white suspension was stirred over night after which it was filtered through a medium frit isolating a white solid reminiscent of LiCl. The filtrate was an orange-yellow solution. Distillation was done at 240 Torr at 50° C. to remove solvent. Upon solvent removal, more LiCl salt precipitated out and was isolated in the amount of 0.24 g. A bulb to bulb vacuum transfer was carried out at <1 Torr and 90° C. to isolate 2.67 g a clear liquid. GC/GC-MS was run of the purified material. TGA/DCS indicates a boiling point at 212.5° C. and 0.70% residual. Stability testing conducted by heating to 80° C. for 3 days showed an average purity decreased from 90.17% to 90.12%.

Example 4: Synthesis of bis(isopropylamino)tert-butoxymethylsilane

To 1.0 g (4.6 mmol) of tris(isopropylamino)methylsilane in 20 mL of hexanes was added 0.34 g (4.6 mmol) of anhydrous tert-butanol. Over the course of a month, gas chromatography mass spectrometry (GC-MS) indicates evidence of desired product with a parent peak of 233 amu. The stability of the compound was not determined.

Comparative Example 1

Synthesis of bis(isopropylamino)ethoxymethylsilane

To 1.0 g (4.6 mmol) of tris(isopropylamino)methylsilane in 20 mL of hexanes was added 0.21 g (4.6 mmol) of anhydrous ethanol. GC-MS indicates desired product with a parent peak of 204 amu. GC-MS and gas chromatography (GC) were run for the reaction mixture after a few days and showed two new peaks had evolved since the last analysis. GC/GC-MS indicates the mixture exists as (in order of increasing retention time) 2 parts of a mystery peak with a parent peak of 148 amu, 4 parts MTES, 1 part isopropylamino-bis-ethoxymethylsilane with a parent peak of 191amu, 2 parts desired product, and 10 parts tris(isopropylamino)methylsilane. This indicates ligand exchange is occurring and that the compound is not stable. By comparison, the compounds in Examples 1-3 having tert-butylamino groups are more stable and would be better precursors.

Comparative Example 2

Synthesis of bis(isopropylamino)isopropoxymethylsilane

Comparative Example

To 145.67 g (670 mmol) of tris(isopropylamino)methylsilane in 1.0 L of hexanes at −20° C. was added 40.27 g (670 mmol) anhydrous isopropyl alcohol. After the course of a month, GC/GC-MS indicates a ratio of 13 to 6 to 43 to 31 tris-isopropoxy to bis-isopropoxy to one isopropoxy substituted to tris(isopropylamino)methylsilane. Like Comparative Example 1, this indicates ligand exchange is occurring and that the compound is not stable.

Example 5: Hydrolysis of bis(tert-butylamino)ethoxymethylsilane in Presence of Isopropyl Alcohol The compound bis(tert-butylamino)ethoxymethylsilane was made as shown in Example 1. One part by volume of bis(tert-butylamino)ethoxymethylsilane was mixed with 10 parts of a solution of 20% water in isopropyl alcohol. The mixture was monitored by GC at one hour after initially mixing and showed complete hydrolysis/condensation of bis-tert-butylaminoethoxymethylsilane had occurred, however, no gelation. The mixture eventually gelled within 16 hours which indicates that the compound would be suitable in a FCVD process due to its rate of hydrolysis/condensation then gelation. Gelation indicates that sufficient cross-linking has occurred to turn the free-flowing liquid into a solid which is an important characteristic for a FCVD precursor.

Example 6: Comparison Between Bis(tert-butylamino)ethoxymethylsilane Spin-Coated Films and Tris-Isopropylaminomethylsilane Films after Aging The compound bis(tert-butylamino)ethoxymethylsilane was made as shown in Example 1. One part by volume of bis(tert-butylamino)ethoxymethylsilane was mixed with four parts of a solution of 20% water in isopropyl alcohol and aged under ambient conditions for two hours before being spun on a silicon wafer using a Laurell WS-400 spin coater at 2000 rpm. The wafer was thermally treated at 150° C. for 10 minutes and analyzed by Fourier Transform Infrared Spectroscopy (FTIR). The film show no deposited Si—OH bonds similar to that of tris-isopropylaminomethylsilane films. Comparative tris-isopropylaminomethylsilane film was made as follows: one part by volume of tris-isopropylaminomethylsilane was mixed with 5 parts of a solution of 20% water in isopropyl alcohol. The mixture was aged for one hour under ambient conditions before being spun on a silicon wafer using a Laurell WS-400 spin coater at 2000 rpm. The tris-isopropylaminomethylsilane film was aged for a shorter amount of time then the bis(tert-butylamino)ethoxymethylsilane film due to its faster rate of hydrolysis/condensation. Wafer was thermally treated at 150° C. for 10 minutes and analyzed by FTIR and showed no deposited Si—OH being indicative that the film is fully cross-linked. The purpose of the comparison was to show that neither films had Si—OH bonds.

Example 7: Hydrolysis of bis(tert-butylamino)ethoxymethylsilane in Presence of Isopropyl Alcohol and Surfynol® 61 (3,5-dimethyl-1-Hexyn-3-ol) Surfactant The compound bis(tert-butylamino)ethoxymethylsilane was made as shown in Example 1. One part by volume of bis(tert-butylamino)ethoxymethylsilane was mixed with four parts of a solution of 20% water in a 1:4 mixture of Surfynol® 61 to isopropyl alcohol. The mixture was aged for two hours under ambient conditions before being spun on a silicon wafer using a Laurell WS-400 spin coater at 2000 rpm. Likewise, one part by volume of bis-tert-butylaminoethoxymethylsilane was mixed with four parts of a solution of 20% water in a 1:1 mixture of Surfynol® 61 to isopropyl alcohol and aged for two hours before being spun as described above in Example 6. The addition of Surfynol® 61 showed no improvement in uniformity of spun films.

Example 8: Hydrolysis of bis(tert-butylamino)ethoxymethylsilane in the Presence of Ethanol The compound bis(tert-butylamino)ethoxymethylsilane was made as shown in Example 1. One part by volume of bis(tert-butylamino)ethoxymethylsilane was mixed with 10 parts of a solution of 20% water in ethanol. The mixture was monitored by GC at one hour after initially mixing and showed complete hydrolysis/condensation of bis-tert-butylaminoethoxymethylsilane had occurred, however, no gelation. The mixture eventually gelled within 16 hours which indicates that the compound would be suitable in a FCVD process due to its rate of hydrolysis/condensation then gelation.

Example 9: Hydrolysis of bis(tert-butylamino)ethoxymethylsilane in the Presence of Ethanol The compound bis(tert-butylamino)ethoxymethylsilane was made as shown in Example 1. One part by volume of bis(tert-butylamino)ethoxymethylsilane was mixed with four parts of a solution of 20% water in ethanol. The mixture was monitored by GC at one hour after initially mixing and showed complete hydrolysis/condensation of bis-tert-butylaminoethoxymethylsilane had occurred, however, no gelation. The mixture eventually gelled within 16 hours which indicates that the compound would be suitable in a FCVD process due to its rate of hydrolysis/condensation then gelation.

Example 10: Hydrolysis of bis(tert-butylamino)ethoxymethylsilane in Presence of Ethanol The compound bis(tert-butylamino)ethoxymethylsilane was made as shown in Example 1. One part by volume of bis-tert-butylaminoethoxymethylsilane was mixed with four parts of a solution of 20% water in ethyl alcohol. The mixture was aged for two hours under ambient conditions before being spun on a silicon wafer using a Laurell WS-400 spin coater at 2000 rpm. The resulting film was a white powder and non-uniform. The present example shows that the addition of alcohol provided different physical characteristics of the spun film.

Example 11: Hydrolysis of bis(tert-butylamino)methoxymethylsilane in Presence of Isopropyl Alcohol The compound bis(tert-butylamino)ethoxymethylsilane was made as shown in Example 2. One part by volume of bis-tert-butylaminomethoxymethylsilane was mixed with 10 parts of a solution of 20% water in isopropyl alcohol. The mixture was monitored by GC at one hour after initially mixing and showed complete hydrolysis/condensation of bis-tert-butylaminomethoxymethylsilane had occurred, however, no gelation. The mixture eventually gelled within 16 hours which indicates that the compound would be suitable in a FCVD process due to its rate of hydrolysis/condensation then gelation.

Example 12: Hydrolysis of bis(tert-butylamino)methoxymethylsilane in Presence of Isopropyl Alcohol The compound bis(tert-butylamino)ethoxymethylsilane was made as shown in Example 2. One part by volume of bis-tert-butylaminomethoxymethylsilane was mixed with four parts of a solution of 20% water in isopropyl alcohol. The mixture was monitored by GC to determine the extent of hydrolysis/condensation of the precursor at 5 minutes, 30 minutes, and 2 hours after initially mixing and showed evidence that a significant amount of bis-tert-butylaminomethoxymethylsilane had undergone hydrolysis/condensation, however, no gelation occurred. The mixture eventually gelled within 16 hours which indicates that the compound would be suitable in a FCVD process due to its rate of hydrolysis/condensation then gelation.

Example 13: Deposition of Flowable Carbon-Doped Silicon Oxynitride Film Using bis(tert-butylamino)methoxymethylsilane The flowable CVD films were deposited onto medium resistivity (8-12 Ωcm) single crystal silicon wafer substrates and silicon pattern wafers. In certain examples, the substrate may be exposed to a pre-deposition treatment such as, but not limited to, a plasma treatment, thermal treatment, chemical treatment, ultraviolet light exposure, electron beam exposure, and/or other treatments to affect one or more properties of the films.

The depositions were performed on an Applied Materials Precision 5000 system in a modified 200 mm DXZ chamber, using either a silane or a TEOS process kit. The PECVD chamber was equipped with direct liquid injection (DLI) delivery capability. The precursors were liquids with delivery temperatures dependent on the precursor's boiling point. To deposit initial flowable nitride films, typical liquid precursor flow rates were 100-5000 mg/min, in-situ plasma power density was 0.25-3.5 W/cm², pressure was 0.75-12 Torr. To densify the as-deposit flowable films, the films were thermally annealed and UV cured in vacuum using the modified PECVD chamber from 100~500° C. or from 300~400° C. Thickness and refractive index (RI) at 632 nm were measured by a SCI reflectometer or Woollam ellipsometer. Typical film thickness ranged from 10 to 2000 nm. Bonding properties hydrogen content (Si—H, C—H and N—H) of the silicon-based films were measured and analyzed by a Nicolet transmission Fourier transform infrared spectroscopy (FTIR) tool. All density measurements were accomplished using X-ray reflectivity (XRR). X-ray Photoelectron Spectroscopy (XPS) and Secondary ion mass spectrometry (SIMS) analysis were performed to determine the elemental composition of the films. The flowability and gap fill effects on patterned wafers were observed by a cross-sectional Scanning Electron Microscopy (SEM) using a Hitachi S-4700 system at a resolution of 2.0 nm.

Flowable CVD depositions were conducted using a design of experiment (DOE) methodology. The experimental design includes: precursor flow from 100 to 5000 mg/min, preferably 1000 to 2000 mg/min; $NH_3$ flow from 100 sccm to 1000 sccm, preferably 100 to 300 sccm; pressure from 0.75 to 12 Torr, preferably 6 to 10 Torr; RF power (13.56 MHz) 100 to 1000 W, preferably 100~500 W; Low-frequency (LF) power 0 to 100 W; and deposition temperature ranged from 0 to 550° C., preferably 0 to 40° C. The DOE experiments were used to determine what process parameters produced the optimal film with good flowability.

In one experiment, the process conditions used to provide the most optimal film properties are as follows: bis(tert-butylamino)methoxymethylsilane flow=1000 mg/min, $NH_3$ flow=0~450 sccm, He=100 sccm, Pressure=8 torr, power=300~600 W, and temperature=30~40° C. On a blanket Si wafer, wet and tacky SiCON films were deposited with the shrinkage ranging from 10% to 50% after thermal annealing and UV cure. Review of cross-sectional scanning electron microscopy (SEM) images showed that bottom-up, seamless, and void-free gap-filling was achieved on pattern wafers, or wafers having at least one surface feature, using bis(tert-butylamino)methoxymethylsilane in a flowable CVD process.

The invention claimed is:

1. A method for forming a silicon-containing film on at least one surface of a substrate comprising:
providing the substrate in a reactor; and
forming the silicon-containing film on the at least one surface by a deposition process using at least one precursor comprising a bisaminoalkoxysilane having Formula I:

$$R^1Si(NR^2R^3)(NR^4R^5)OR^6 \qquad I$$

wherein $R^1$ is a methyl group; $R^2$ and $R^4$ are each hydrogen atoms; $R^3$ and $R^5$ are each selected from tert-butyl and tert-pentyl; and $R^6$ is selected from a $C_1$ to $C_3$ linear alkyl group and a $C_3$ to $C_5$ branched alkyl group.

2. The method of claim 1, wherein the deposition process is selected from the group consisting of cyclic chemical vapor deposition (CCVD), thermal chemical vapor deposition, plasma enhanced chemical vapor deposition (PECVD), high density PECVD, photon assisted CVD, plasma-photon assisted (PPECVD), cryogenic chemical vapor deposition, chemical assisted vapor deposition, hot-filament chemical vapor deposition, CVD of a liquid polymer precursor, low energy CVD (LECVD), and flowable chemical vapor deposition.

3. The process of claim 2, wherein the deposition process is flowable chemical vapor deposition (FCVD).

4. The method of claim 1 wherein the at least one precursor comprising a bisaminoalkoxysilane having Formula I is at least one selected from the group consisting of bis(tert-butylamino)methoxymethylsilane, bis(tert-butylamino)ethoxymethylsilane, and bis(tert-butylamino)isoproxymethylsilane.

5. The method of claim 1 wherein the at least one precursor comprising a bisaminoalkoxysilane having Formula I comprises bis(tert-butylamino)ethoxymethylsilane.

6. A method for depositing a silicon-containing film on at least a portion of a substrate having a surface feature in a flowable chemical vapor deposition process, the method comprising the steps of:
placing a substrate having a surface feature into a reactor wherein the reactor is maintained at one or more temperatures ranging from −20° C. to about 400° C.;
introducing into the reactor at least one precursor comprising a bisaminoalkoxysilane compound having a Formula I:

$$R^1Si(NR^2R^3)(NR^4R^5)OR^6 \qquad I$$

wherein $R^1$ is a methyl group; $R^2$ and $R^4$ are each hydrogen atoms; $R^3$ and $R^5$ are each selected from tert-butyl and tert-pentyl; and $R^6$ is selected from a $C_1$ to $C_3$ linear alkyl group and a $C_3$ to $C_5$ branched alkyl group;
introducing a source selected from an oxygen source, a nitrogen-containing source, or both to react with the bisaminoalkoxysilane compound on the substrate to form a flowable film on at least a portion of the surface feature;
treating the flowable film with an oxygen source at one or more temperatures ranging from about 100° C. to about 1000° C. to form a solid silicon and oxygen containing film on at least a portion of the surface feature.

7. The method of claim 6 further comprising exposing the flowable film to ultraviolet irradiation at one or more temperatures ranging from about 100° C. to about 1000° C.

8. The method of claim 6 wherein at least one of the oxygen sources is selected from the group consisting of water, oxygen plasma, ozone, and a combination thereof.

9. The method of claim 6 wherein the nitrogen-containing source is selected from the group consisting of ammonia, hydrazine, monoalkylhydrazine, dialkylhydrazine, organic amines, a plasma comprising nitrogen and hydrogen, ammonia plasma, nitrogen plasma, and organic amine plasma.

10. The method of claim 6 wherein the steps can be repeated until the surface feature is substantially filled with the solid silicon and oxygen containing film.

11. The method of claim 6 wherein the at least one precursor comprising a bisaminoalkoxysilane having Formula I is at least one selected from the group consisting of bis(tert-butylamino)methoxymethylsilane, bis(tert-butylamino)ethoxymethylsilane, and bis(tert-butylamino)isoproxymethylsilane.

12. The method of claim 6 wherein the at least one precursor comprising a bisaminoalkoxysilane having Formula I comprises bis(tert-butylamino)ethoxymethylsilane.

13. The method of claim 6 wherein the reactor is maintained at one or more temperatures ranging from 0° C. to about 40° C.

* * * * *